United States Patent
Lin et al.

(10) Patent No.: US 9,005,922 B2
(45) Date of Patent: Apr. 14, 2015

(54) SENSOR CHIP FOR SCREENING TOPOISOMERASE INHIBITOR AND SCREENING METHOD THEREOF

(75) Inventors: Chun-Mao Lin, Cishan Township (TW); Hsiang-Ping Tsai, Taipei (TW); Chwen-Ming Shih, Sijhih (TW); Jau-Lang Hwang, Taichung (TW); Chi-Ming Lee, Tucheng (TW)

(73) Assignee: Taipei Medical University, Taipei (TW)

( * ) Notice: Subject to any disclaimer, the term of this patent is extended or adjusted under 35 U.S.C. 154(b) by 607 days.

(21) Appl. No.: 12/924,118

(22) Filed: Sep. 21, 2010

(65) Prior Publication Data

US 2011/0287438 A1 Nov. 24, 2011

(30) Foreign Application Priority Data

May 24, 2010 (TW) .............................. 99116573 A

(51) Int. Cl.
*C12N 15/09* (2006.01)
*G01N 33/573* (2006.01)
*C12Q 1/533* (2006.01)

(52) U.S. Cl.
CPC .............. *G01N 33/573* (2013.01); *C12Q 1/533* (2013.01); *G01N 2500/00* (2013.01)

(58) Field of Classification Search
None
See application file for complete search history.

(56) References Cited

U.S. PATENT DOCUMENTS 6,620,588 B1 * 9/2003 Bushman et al. .............. 435/7.1
6,808,938 B2 * 10/2004 Hamalainen et al. ......... 436/518

OTHER PUBLICATIONS

Syrovets, T., et al., Acetyl-Bosewellic Acids Are Novel Catalytic Inhibitors of Human Topoisomerases I and IIa, Molecular Pharmacology, vol. 58, No. 1, pp. 71-81, 2000.
Taiwanese Official Action dated Oct. 22, 2012.

* cited by examiner

*Primary Examiner* — Richard Hutson
(74) *Attorney, Agent, or Firm* — Hudak, Shunk & Farine Co. LPA

(57) ABSTRACT

The present invention discloses a sensor chip for screening a topoisomerase inhibitor and a screening method thereof. The sensor chip comprises topoisomerase I and a biochip. The topoisomerase I is immobilized on the biochip, and the topoisomerase I has DNA catalytic activity. This provides a rapid screening method for topoisomerase I inhibitors.

7 Claims, 9 Drawing Sheets

SENSOR CHIP FOR SCREENING TOPOISOMERASE INHIBITOR AND SCREENING METHOD THEREOF

FIELD OF THE INVENTION

The present invention relates to a sensor chip and a method thereof; and more particularly, to a sensor chip for screening a topoisomerase inhibitor and a screening method thereof. The sensor chip comprises a micro-fluid chip immobilized with topoisomerase, and can be a platform for screening topoisomerase inhibitors.

BACKGROUND OF THE INVENTION

For acting enzymes on deoxyribonucleic acid (DNA) transcription and replication, the double stranded DNA must be cleaved by helicase firstly. Topoisomerase could cut double-stranded supercoiled DNA to change the DNA conformation, then connecting the original cleavage sites of the DNA. The topoisomerase comprises topoisomerase I (Top I) and topoisomerase II (Top II). The Top I cuts one strand of double-stranded supercoiled DNA via destroying phosphodiester bonds to form a small nick. In the meanwhile, the other strand of the double-stranded supercoiled DNA can pass through the nick for re-ligation. Both strands of double-stranded DNA can be cleaved by the Top II and then religated by changing the DNA conformation.

At the rapid multiplication phase of cells, the high concentration and hyperactivity of the topoisomerase are presented. Thus, anti-cancer drugs can be developed by pharmacists via inhibiting the topoisomerase activity to inhibit or block the growth of cancer cells at slow or rapid multiplication phase. The topoisomerase activity must be relied on during the life cycles of immune cells or pathogenic infection sources, such as virus, bacteria or protozoa. If there are inhibitors to interfere the topoisomerase activity, the life of the aforesaid cells can be affected. Previous studies have indicated that topoisomerase inhibitors are applied to anti-tumor, anti-infection sources, whose infection sources are such as virus, bacteria and etc., anti-inflammatory and immune regulation fields. There is effort to study in the synthesis and research of the topoisomerase inhibitors in the pharmaceutical industry.

Traditionally, the topoisomerase inhibitors is analyzed by a gel electrophoresis or cell responses, but the drawbacks thereof are time consuming. Alternatively, the enzyme inhibitors are analyzed by a 3D computer-aided molecular modeling. The results obtained from the 3D computer-aided molecular modeling do not represent real enzyme responses, and thus the obtained results are inconsistent with the results of the actual enzyme activity. Recently, the topoisomerase inhibitor activity can be effectively detected by chip techniques. Using the chip techniques for screening topoisomerase inhibitors can increase greatly performance. Especially, the micro-fluid chip development can be more convenient and rapid for studying in the dynamic analysis of the topoisomerase inhibitors. Before the present invention is disclosed, substances immobilized onto chips are DNA or inhibitors, and topoisomerase is used as a mobile phase and injected into the chip immobilized with DNA or inhibitors to be analyzed. However, the results thereof are often to cause large consumption of the topoisomerase. Additionally, steps and important notices for purifying the topoisomerase having catalytic activity are more complicated than those of DNA. When the topoisomerase is used as the mobile phase, the experiment results must be considered with variables during purifying the topoisomerase. The catalytic activity of proteins is not easy to maintain, and the proteins are degraded easily, such that the screening purpose is not reached quickly. Furthermore, a DNA molecule often has a plurality of biding sites for the topoisomerase, and the topoisomerase has different affinities on different biding sites so as to increase the variables with regard to determine affinity constants, which results in analyzing incorrectly while testing the dynamic analysis. A person having ordinary skill in the art hopes to effectively resolve the difficulty.

SUMMARY OF THE INVENTION

In view of the aforementioned drawbacks in prior art, an object of the present invention is to provide a sensor chip for screening a topoiomerase inhibitor and a screening method thereof, so as to achieve the rapid and convenient efficiency for inhibitor screening.

To achieve the above object, the sensor chip for screening a topoisomerase inhibitor according to the present invention comprises a biochip and topoisomerase. The topoisomerase is immobilized on the biochip. The biochip may be a micro-fluid chip and the topoisomerase may be topoisomerase I (Top I) or topoisomerase II (Top II). The topoisomerase may be extracted from virus, bacteria, fungi, protozoa, parasites, animal cells, plant cells or human cells. When the topoisomerase immobilized on the biochip is the Top I, the biochip can screen Top I inhibitors, such as a camptothecin (CPT) or derivatives thereof.

In addition, the screening method for a topoisomerase inhibitor comprises the following steps. An inhibitor to be analyzed is added onto the sensor chip as above description. Further, the binding activity between the inhibitor to be analyzed and the topoisomerase is detected by a surface plasmon resonance (SPR) assay.

Furthermore, the topoisomerase immobilized on the biochip in the present invention has catalytic activity to change the DNA conformation. When DNA and an inhibitor to be analyzed are simultaneously added into the biochip, the topoisomerase binds to the DNA to form a topoisomerase-DNA cleavage complex. The binding activity between the inhibitor to be analyzed and the topoisomerase-DNA cleavage complex can be detected via the SPR assay. That is, the variation of resonance units (RUs) obtained from the SPR assay is used to reflect the inhibitory activities. The inhibitors are potentially applied to block the DNA transcription, replication or recombination.

Accordingly, the sensor chip for screening a topoisomerase inhibitor and the screening method thereof according to the present invention provide one or more of the following advantages:

(1) Because the sensor chip of the present invention uses the SPR assay to screen analytes, the analytes do not label with any fluorescent or radioactive substances, such that the biding activity of the analytes and ligands can be detected directly in real-time.

(2) The topoisomerase immobilized on sensor chip of the present invention has DNA catalytic activity comprising that the topoisomerase can bind to supercoiled DNA to form a topoisomerase-DNA cleavage complex, and then the inhibitor to be analyzed binds thereon, thereby validating the inhibitor is the topoisomerase inhibitor.

(3) In the present invention, the topoisomerase is immobilized on the biochip as a stationary phase, which can not only decrease protein consumption during the operating process, but decrease the difficulty of counting variables due to a single activity site thereon while detecting the topoisomerase binds to an inhibitor to be analyzed or a topoisomerase-DNA cleavage complex.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENTS

The present invention will now be described with some preferred embodiments thereof with reference to the accompanying drawings. It is understood the experimental data shown in the embodiments are provided only for easy interpretation of the technical means of the present invention and should in no means be considered as restriction to the present invention.

The sensor chip for screening a topoisomerase inhibitor according to the present invention comprises a biochip and topoisomerase. The topoisomerase is immobilized on the biochip. The topoisomerase has DNA catalytic activity.

When DNA and an inhibitor to be analyzed are simultaneously injected into the sensor chip, the DNA binds to the topoisomerase to form a topoisomerase-DNA cleavage complex. The binding activity between the inhibitor to be analyzed and the topoisomerase-DNA cleavage complex can be detected via the surface plasmon resonance (SPR) assay. That is, the variation of resonance units obtained from the SPR assay is used to confirm whether the inhibitor to be analyzed has anti-topoisomerase activity or not.

The topoisomerase may be topoisomerase I (Top I) or topoisomerase II (Top II). The types of the biochip may be selected according to the SPR assay, and the biochip may be a micro-fluid chip. When the Top I is immobilized on the biochip, Top I inhibitors, such as a camptothecin or derivatives thereof, can be detected. When the Top II is immobilized on the biochip, Top II inhibitors, such as an etoposide (VP-16) or derivatives thereof, can be detected.

Figure 1:
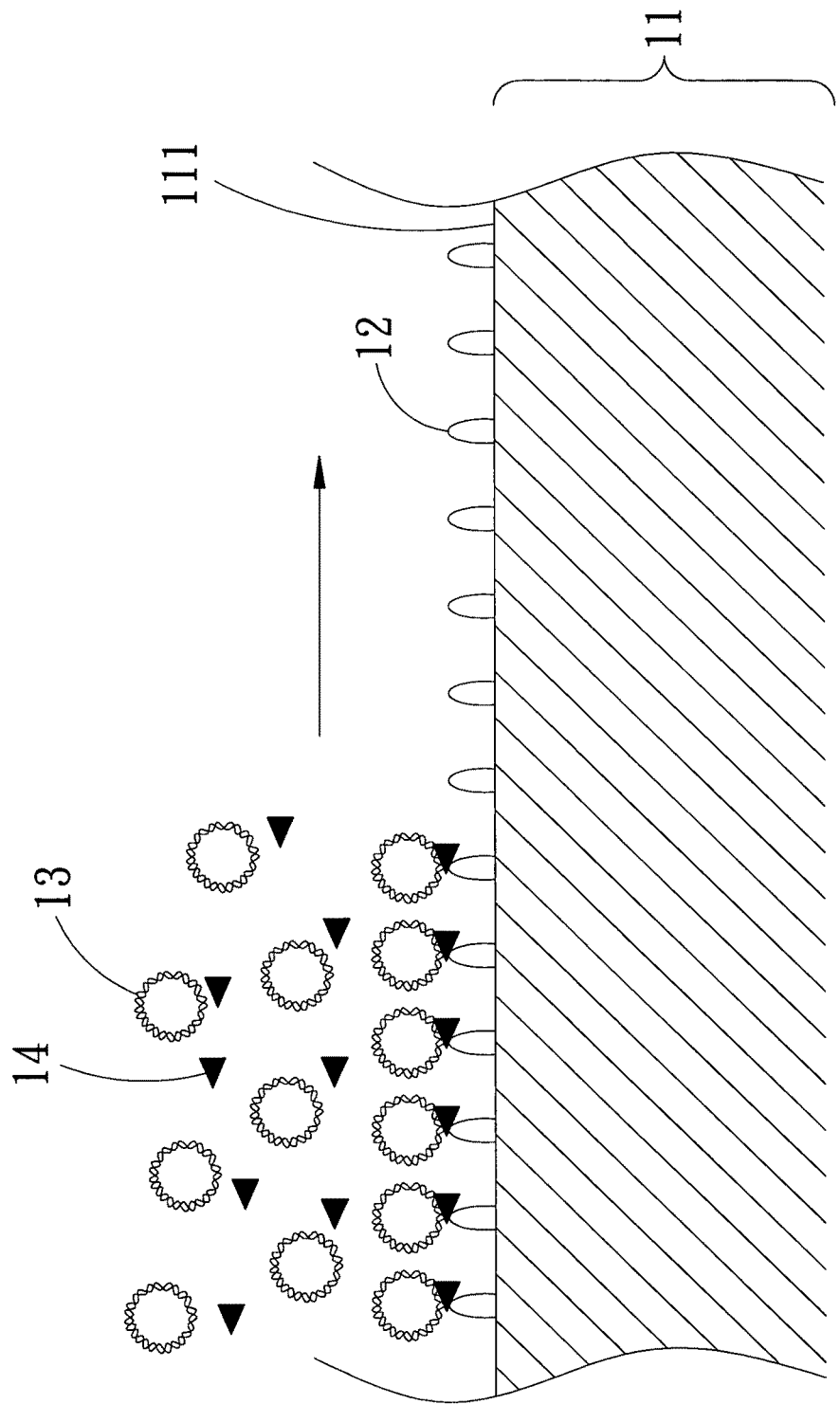
FIG. 1 is a sectional diagram of a sensor chip for screening a topoisomerase inhibitor according to an embodiment of the present invention.

Please refer to FIG. 1 that is a sectional diagram of a sensor chip for screening a topoisomerase inhibitor according to an embodiment of the present invention. As shown, the biochip in the present embodiment is a micro-fluid chip 11, and the Top I 12 is immobilized on the surface of the micro-fluid channel 111. Top I 12 has the DNA catalytic activity to change the DNA conformation. Thus, when analytes comprising supercoiled DNA and inhibitors 14 to be detected are simultaneously injected into the micro-fluid channel 111 of the sensor chip according to the present invention, DNA conformation can be changed by the Top I 12 to form a Top I-DNA cleavage complex. The arrow in FIG. 1 represents the flow direction of the analytes. The resonance units obtained from the SPR assay are used to reflect inhibitors 14 binding to the Top I-DNA cleavage complex. When the inhibitors 14 bind to the Top I-DNA cleavage complex, the inhibitors 14 are anti-Top I drugs.

Figure 2:
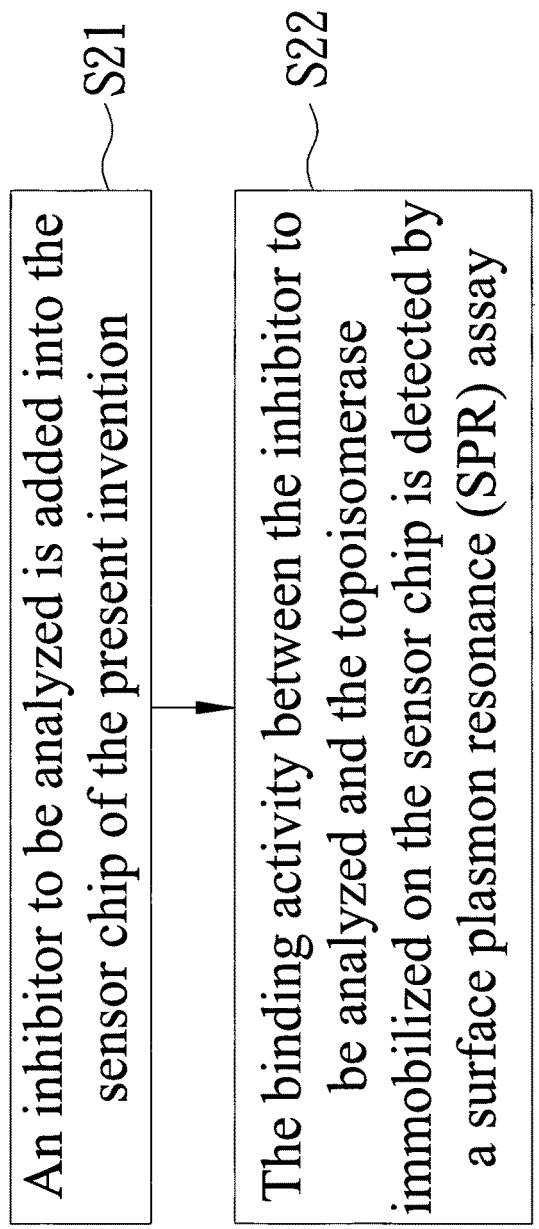
FIG. 2 is a flowchart of a screening method for a topoisomerase inhibitor according to the present invention.

Please refer to FIG. 2 that is a flowchart of a screening method for a topoisomerase inhibitor according to the present invention. As shown, an inhibitor to be analyzed is added into the sensor chip of the present invention in the step S21. In the step S22, the binding activity between the inhibitor to be analyzed and the topoisomerase immobilized on the sensor chip is detected by a surface plasmon resonance (SPR) assay. The binding activity is represented by a variation of resonance units obtained from the SPR assay. Additionally, DNA may be added into the sensor chip of the present invention together with the inhibitor to be analyzed. The topoisomerase on the sensor chip of the present invention has DNA catalytic activity to bind to the DNA to form a topoisomerase-DNA cleavage complex. The SPR assay is used to detect whether the inhibitor to be analyzed binds to the topoisomerase-DNA cleavage complex or not. When the inhibitor to be analyzed binds to the topoisomerase-DNA cleavage complex, the inhibitor has anti-topoisomerase activity, so as to block the DNA transcription, replication or recombination.

Figure 3:
FIG. 3 illustrates recombinant human topoisomerase I (hTop I) verified by a Western blot analysis in the present invention.

A baculovirus expression system is utilized as one of expression systems for expressing exogenous proteins in quantity. In the present embodiment, the baculovirus expression system is used to produce the recombinant human Top I, which is abbreviated "hTop I" below, and the hTop I has the DNA catalytic activity. A Western blot analysis is used to verify that the purified protein is the hTop I actually, as sown in FIG. 3, which shows that the concentrations of the hTop I are 20, 10 and 5 μg from left to right, respectively.

In the present embodiment, the inhibitor to be analyzed may be a camptothecin (CPT). The anti-cancer mechanism of the CPT is to stabilize the Top I-DNA cleavage complex, such that the DNA does not perform the re-ligation reaction thereby blocking the DNA recombination or replication. The pUC19 plasmid DNA is used as the supercoiled DNA in the present embodiment.

Figure 4:
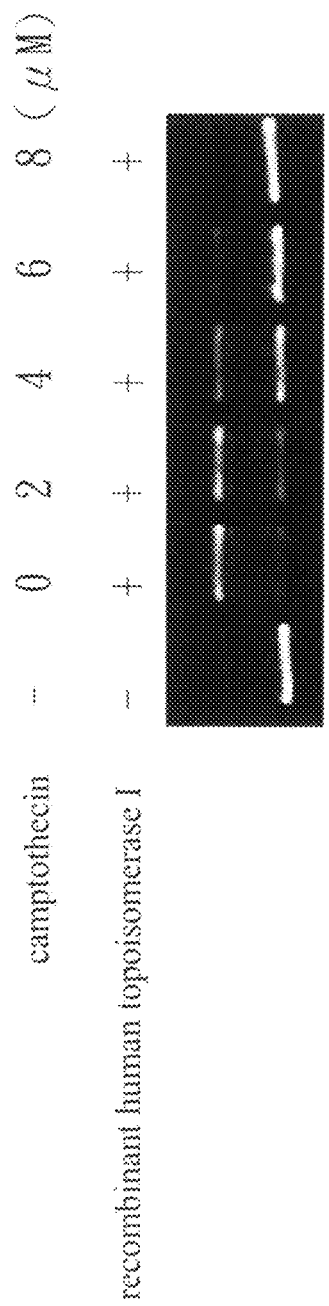
FIG. 4 is a DNA eletropherogram illustrating inhibitory activity of a camptothecin on the r hTop I and pUC19 plasmid DNA.

The pUC19 plasmid DNA is closely circular double-stranded supercoiled DNA. When the pUC19 plasmid DNA is interacted with the Top I, one strand of the circular double-stranded supercoiled DNA is cleaved, separated and religated to form a relaxed form. A gel electrophoresis assay is used to evaluate the conformational change of pUC19 plasmid DNA. The inhibitory effect of the CPT on the supercoiled DNA breakage caused by hTop I is also evaluated. The results are shown in FIG. 4. The supercoiled DNA (FIG. 4, lane 1) migrates faster than the relaxed circular DNA (FIG. 4, lane 2) on the agarose gel. Specifically, lane 1 of FIG. 4 represents "pUC19 plasmid DNA only", and lane 2 of FIG. 4 represents "the pUC19 plasmid DNA with hTop I." Furthermore, the CPT inhibits the relaxed structure caused by the hTop I. Thus, CPT treatment inhibited hTop I relaxation activity, and a greater amount of uncatalytic supercoiled DNA is retained in a concentration-dependent manner (FIG. 4, lanes 3-6, 2-8 μM).

Figure 5:
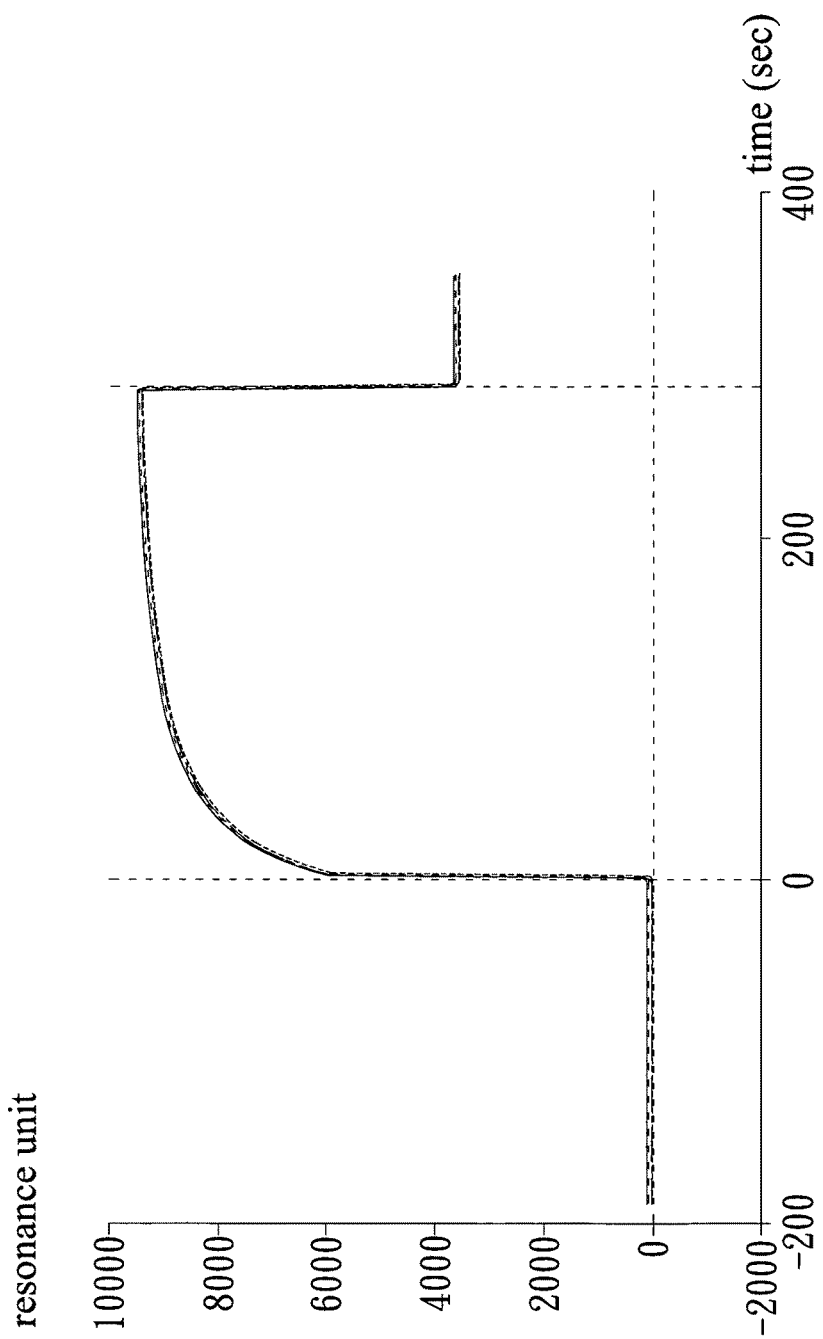
FIG. 5 is a surface plasmon resonance (SPR) sensorgram illustrating the hTop I is immobilized on the biochip of the present invention.
Figure 6:
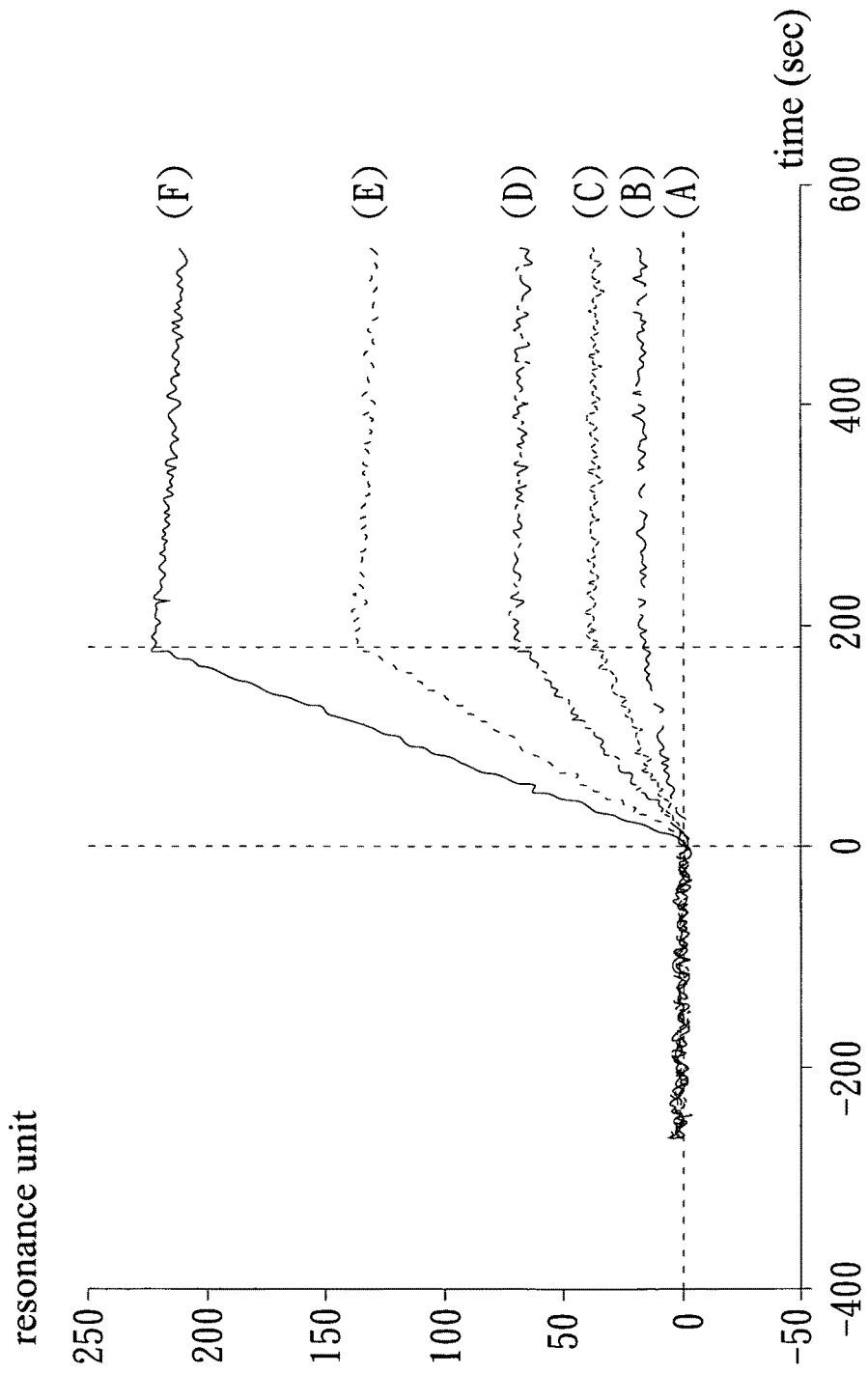
FIG. 6 is a SPR sensorgram illustrating the hTop I immobilized on the biochip binds with diluted polyclonal antibodies against the hTop I.

The aforementioned results verify the purified hTop I, the pUC19 plasmid DNA and the CPT in the present embodiment have their own activity, and thus the hTop I is used to immobilize on the carboxymethylated dextran surface of the micro-fluid chip in the present embodiment (not limited thereto). Briefly, the surface of the micro-fluid chip is activated with 0.05-0.5 M N-hydroxysuccinimide and 0.1-0.5 M N-ethyl-N'-(3-dimethylaminopropyl) carbodiimimide at a flow rate of 25 μL/min. The hTop I is diluted in 10 mM sodium acetate and adjusted pH values to pH 3.0-10.0, preferably to pH 5.0-8.5, especially to pH 7.5. The hTop I is immobilized on the micro-fluid chip at 20-40☐ (preferably at 25☐) using a flow rate of 10-40 μL/min (preferably 25-30 μL/min, specially 25 μL/min) for 60-300 seconds (preferably 200-300 seconds), and therefore the contents of the hTop I are about 20-150 μL. Activated amine groups are quenched with injecting 1 M ethanolamine (pH 7.0-9.0). Recombinant hTop I was covalently coupled to the carboxymethylated dextran surface of the chip using standard amine-coupling chemistry. The immobilization curves are shown in FIG. 5, which shows that the highest level of the hTop I immobilized on the micro-fluid chip is achieved at 4000 resonance units (RUs). Additionally, the binding of anti-hTop I antibodies to immobilized hTop I is observed in real time after reference subtraction of the response from the hTop I control. The response is proportional to the antibody concentration, as shown in FIG. 6. As shown, the curves (A), (B), (C), (D), (E) and (F) illustrates 0, 1, 2, 4, 8 and 16 times diluted concentration of the anti-hTop I antibodies, respectively. The results show the binding affinity between the hTop I and the anti-hTop I antibodies has a concentration-dependent manner.

Figure 7:
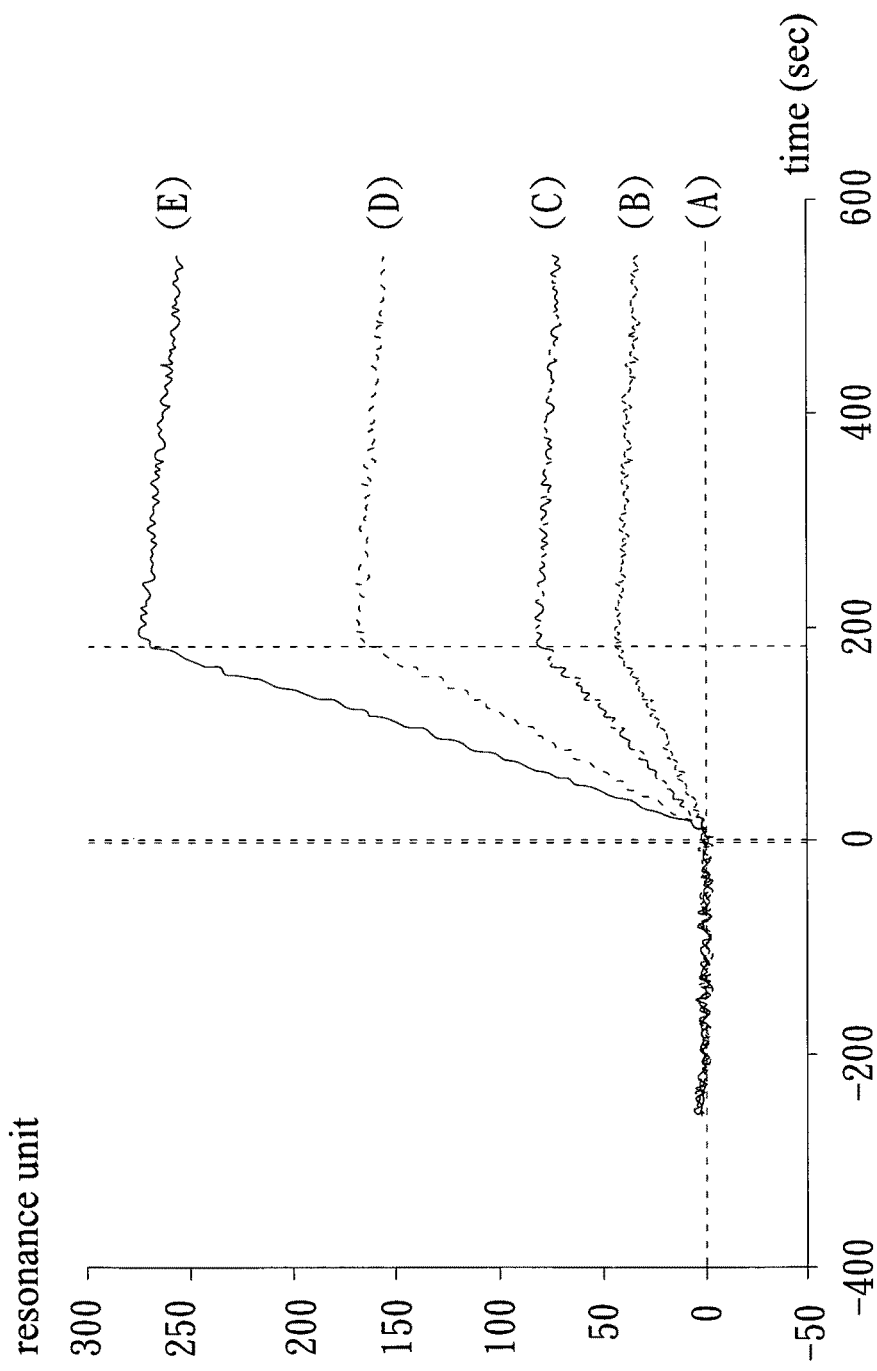
FIG. 7 is a SPR sensorgram illustrating the interaction between the immobilized hTop I and the pUC19 plasmid DNA.

When the pUC19 plasmid DNA is loaded onto the micro-fluid chip immobilizing the hTop I, the binding affinities between the pUC19 plasmid DNA and the hTop I is measured by the SPR assay. The binding of the pUC19 plasmid to immobilized hTop I is detected and shows the concentration-dependent increase in RU, as shown in FIG. 7. The concentrations of the pUC19 plasmid DNA illustrating the curves (A), (B), (C), (D), (E) and (F) in FIG. 7 are 0, 125, 250, 500 and 1000 ng/ml, respectively. To sum up said results, the hTop I immobilized on the micro-fluid chip retains its DNA-binding activity.

Figure 8:
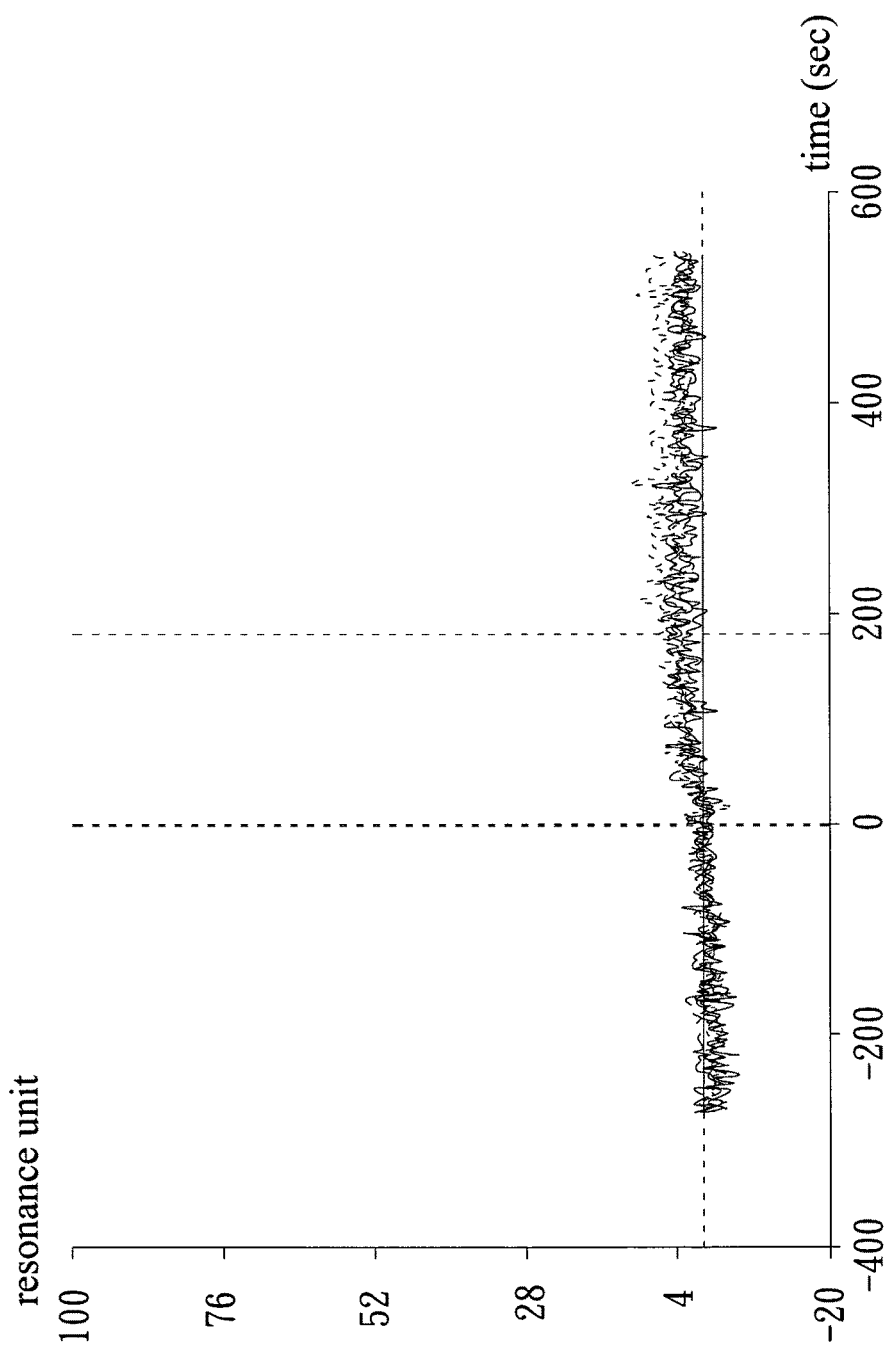
FIG. 8 is a SPR sensorgram illustrating the interaction between the camptothecin and the immobilized hTop I without the pUC19 plasmid DNA in analytes.
Figure 9:
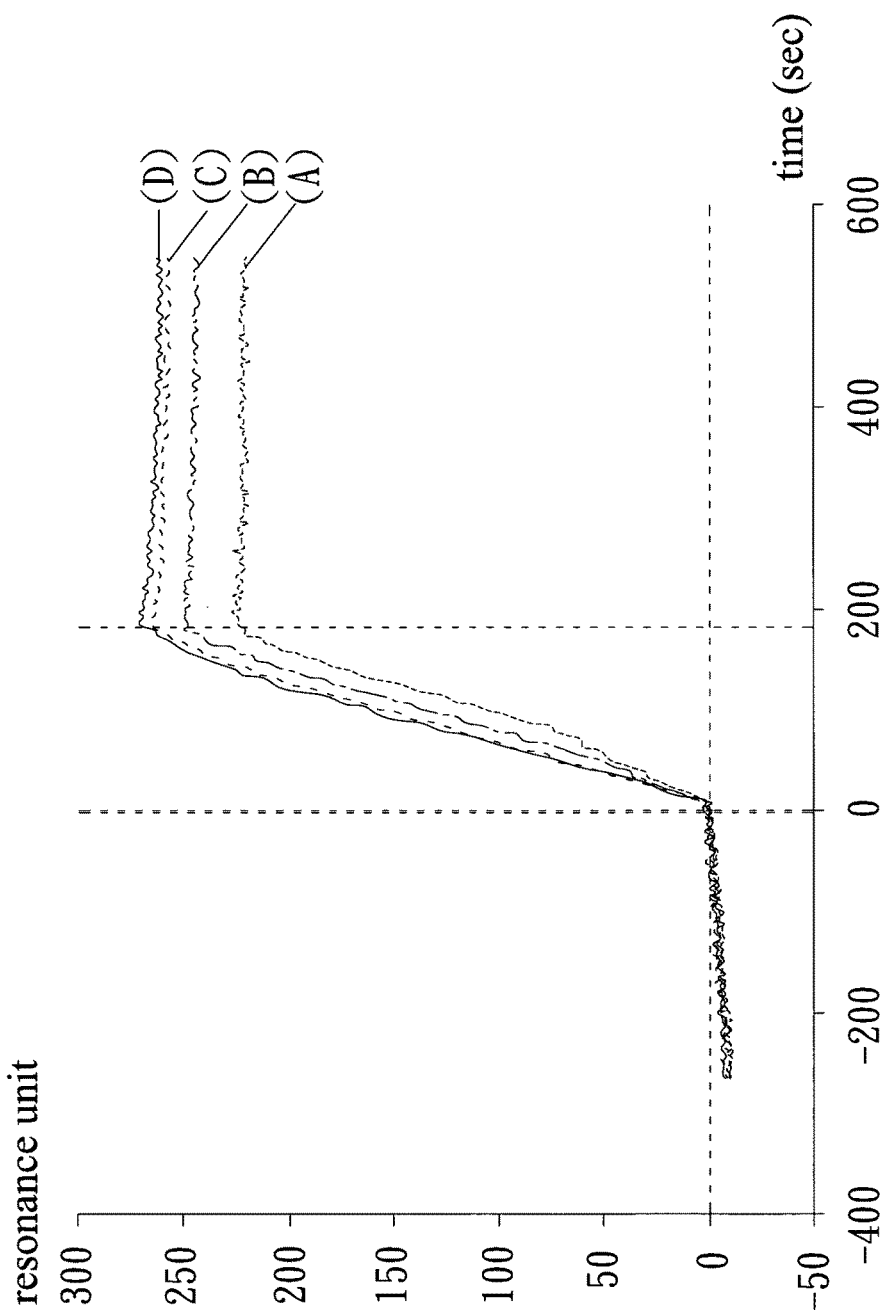
FIG. 9 is a SPR sensorgram illustrating the interaction between the camptothecin and the immobilized hTop I with the pUC19 plasmid DNA in analytes.

RU values of CPT alone (0-250 nM) in the analytes flowing through the sensor chip of the present invention remains fairly constant, as shown in FIG. 8, which indicates that CPT does not bind to hTopI without DNA. It proves that the binding of CPT to hTop I on the micro-fluid chip is dependent on the DNA content because CPT binds to hTopI at the stage of forming intermediates of the hTopI-DNA cleavage complex. To characterize the drug-binding kinetics using the SPR sensor chip, plasmid DNA (1.0 μg/ml) is included in the analytes. The combination of pUC19 plasmid DNA and CPT (0, 62.5, 125 and 250 nM) as the analyte is measured flowing through the sensor chip of the present invention, and the RU increases in a concentration-dependent manner (FIG. 9) with a KD value of $4.1 \times 10^{-29}$ (Ka=$9.11 \times 10^7$, Kd=$3.74 \times 10^{-21}$) compared to DNA only, according to the ProteOn Manager 2.0 calculation. In the presence of the hTop I inhibitor and CPT, re-ligation is impeded; and DNA and hTop I are trapped in a covalent cleavage complex. 0, 62.5, 125 and 250 nM of CPT reflect in the curve (A), (B), (C) and (D) of FIG. 9, respectively. The interaction causes an increase in the higher the mass of ligands immobilized on the micro-fluid chip, and is reflected in a rise in RUs. When a Top II inhibitor, VP-16, and the pUC19 plasmid DNA simultaneously are loaded onto the micro-fluid chip of the present invention, the VP-16 does not bind to the hTop I immobilized on the micro-fluid chip. The result shows the hTop I immobilized on micro-fluid chip of the present invention has the binding specificity. From the foregoing, the conformation and binding activity of enzymes can be maintained. Furthermore, the SPR assay can detect whether inhibitors to be analyzed are anti-topoisomerase drugs or not in real time.

The SPR assay is used to detect interactions between proteins and DNA in the aforementioned embodiments. The advantages of the SPR assay comprise: analytes do not label with any fluorescent or radioactive substances, such that the biding activity of the analytes and ligands can be detected directly in real-time. Thus, the binding activity between inhibitors to be analyzed and DNA, or between inhibitors to be analyzed and topoisomerase-DNA cleavage complexes is detected by SPR assay, and the topoisomerase, the DNA or the inhibitors to be analyzed does not be labeled with any substances, such as fluorescent or radioactive substances, to read data. Furthermore, the SPR assay can directly detect whether inhibitors to be analyzed are anti-topoisomerase drugs or not in real time, and the sensor chip of the present invention can also ensure the reliability of binding kinetic studies of Top I.

The present invention has been described with some preferred embodiments thereof and it is understood that many changes and modifications in the described embodiments can be carried out without departing from the scope and the spirit of the invention that is intended to be limited only by the appended claims.

What is claimed is:

1. A screening method for a topoisomerase inhibitor, comprising the following steps:
    immobilizing a topoisomerase, on a micro-fluid chip, by flowing through a solution comprising the topoisomerase with a flow rate of 10-40 μL/min for 60-300 seconds, wherein a pH value of the solution ranges from 3.0-10.0;
    adding deoxyribonucleic acid and an inhibitor to be analyzed onto the micro-fluid chip comprising the immobilized topoisomerase; and
    detecting a binding activity of the inhibitor to be analyzed and the immobilized topoisomerase by a surface plasmon resonance assay.

2. The screening method as claimed in claim 1, wherein the deoxyribonucleic acid and the topoisomerase form a topoisomerase-deoxyribonucleic acid cleavage complex.

3. The screening method as claimed in claim 2, further comprising a step of determining the binding activity of the inhibitor to be analyzed and the topoisomerase-deoxyribonucleic acid cleavage complex by the surface plasmon resonance assay.

4. The screening method as claimed in claim 1, wherein the binding activity is represented by a variation of resonance units obtained from the surface plasmon resonance assay.

5. The screening method as claimed in claim 1, wherein the topoisomerase comprises topoisomerase I.

6. The screening method as claimed in claim 5, wherein the topoisomerase further comprises human topoisomerase I.

7. The screening method as claimed in claim 5, wherein the inhibitor comprises a camptothecin and derivatives thereof.

* * * * *